(12) United States Patent
Zhang et al.

(10) Patent No.: US 9,714,927 B2
(45) Date of Patent: Jul. 25, 2017

(54) MEDICAL EQUIPMENT FOR GAS MONITORING

(71) Applicant: Shenzhen Mindray Bio-Medical Electronics Co., Ltd., Shenzhen (CN)

(72) Inventors: Xuegang Zhang, Shenzhen (CN); Zhonghua Liu, Shenzhen (CN); Guangqi Huang, Shenzhen (CN); Meng Zhu, Shenzhen (CN); Jian Cen, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 540 days.

(21) Appl. No.: 14/334,439

(22) Filed: Jul. 17, 2014

(65) Prior Publication Data

US 2014/0326041 A1    Nov. 6, 2014

Related U.S. Application Data

(63) Continuation of application No. PCT/CN2012/087487, filed on Dec. 26, 2012.

(30) Foreign Application Priority Data

Jan. 19, 2012    (CN) .......................... 2012 1 0017608

(51) Int. Cl.
  *B01D 53/02*        (2006.01)
  *G01N 33/00*        (2006.01)
  (Continued)

(52) U.S. Cl.
  CPC ....... *G01N 33/0036* (2013.01); *A61B 5/0836* (2013.01); *A61M 16/085* (2014.02);
  (Continued)

(58) Field of Classification Search
  CPC . A61B 5/0836; A61M 16/0003; A61M 16/01; A61M 16/085; A61M 16/104;
  (Continued)

(56) References Cited

U.S. PATENT DOCUMENTS 4,546,778 A    10/1985 Sullivan
5,326,973 A *   7/1994 Eckerbom .............. G01N 21/05
                                                           250/343

(Continued)

FOREIGN PATENT DOCUMENTS

CN    101518664 A    9/2009
CN    101636110 A    1/2010
(Continued)

*Primary Examiner* — Christopher P Jones
(74) *Attorney, Agent, or Firm* — Kory D. Christensen; Polsinelli LLP

(57) ABSTRACT

Provided is medical equipment for gas monitoring having a gas treatment system, including a first gas monitoring module and an integrated gas circuit board. A first gas circuit that may be a through passage with both inlet and outlet can be arranged inside the integrated gas circuit board. A gas outlet, at least one gas inlet and at least one monitoring interface can be arranged on a surface of the integrated gas circuit board. The gas inlet may include a first gas inlet, and the first gas inlet and the gas outlet can communicate with two ends of the first gas circuit. The monitoring interface may include a first monitoring interface for communication between the first gas circuit and the first gas monitoring module, and an internal gas inlet interface and an internal gas outlet interface for communication between the first gas circuit and a second internal gas monitoring module.

15 Claims, 5 Drawing Sheets

(51) Int. Cl.
*A61M 16/08* (2006.01)
*A61B 5/083* (2006.01)
*A61M 16/01* (2006.01)
*A61M 16/10* (2006.01)

(52) U.S. Cl.
CPC ........... *A61M 16/01* (2013.01); *A61M 16/104* (2013.01); *A61M 2016/1025* (2013.01); *A61M 2016/1035* (2013.01); *A61M 2230/432* (2013.01)

(58) Field of Classification Search
CPC .. A61M 2016/1025; A61M 2016/1035; A61M 2230/432; G01N 33/0006; G01N 33/0009; G05D 7/0635
See application file for complete search history.

(56) References Cited

U.S. PATENT DOCUMENTS

| | | | | |
|---|---|---|---|---|
| 2008/0142019 | A1* | 6/2008 | Lewis | A61J 7/0053 128/207.18 |
| 2009/0062673 | A1* | 3/2009 | Scampoli | A61B 5/087 600/529 |
| 2010/0294021 | A1* | 11/2010 | Makino | G01N 25/18 73/25.03 |
| 2011/0100362 | A1* | 5/2011 | Baecke | A61M 16/12 128/203.12 |
| 2011/0155131 | A1* | 6/2011 | Bottom | A61M 16/104 128/203.14 |
| 2015/0075522 | A1* | 3/2015 | Acker | A61M 16/0051 128/202.22 |

FOREIGN PATENT DOCUMENTS

| | | |
|---|---|---|
| CN | 101784229 A | 7/2010 |
| CN | 102107037 A | 6/2011 |
| CN | 202010339 U | 10/2011 |
| CN | 102266619 A | 12/2011 |

* cited by examiner

MEDICAL EQUIPMENT FOR GAS MONITORING

CROSS-REFERENCE

This application is a continuation of Patent Cooperation Treaty Application No. PCT/CN2012/087487, filed Dec. 26, 2012, which is hereby incorporated by reference.

TECHNICAL FIELD

This disclosure relates generally to medical equipment and particularly to medical equipment for gas monitoring.

BACKGROUND

During medical treatments, a gas concentration monitoring module for anesthetic gas and carbon dioxide ($CO_2$) may often be used to monitor an anesthetic gas concentration and a $CO_2$ concentration in a gas sample extracted from a patient. Specifically, an anesthetic gas monitoring probe (GMB probe) may be arranged in a gas sampling circuit for anesthetic gas in the gas concentration monitoring module for anesthetic gas and $CO_2$. When the anesthetic gas enters into the gas concentration monitoring module through the gas sampling circuit, the GMB probe can monitor the anesthetic gas concentration and the $CO_2$ concentration as needed.

In clinical practice, some other gas treatments may also be needed in addition to the monitoring of the anesthetic gas concentration and the $CO_2$ concentration. For example, an oxygen concentration monitoring module may be utilized for oxygen concentration monitoring, or a respiratory mechanics module may be used for monitoring respiratory mechanics parameters including gas pressure and differential gas pressure. In such cases, the gas concentration monitoring module for anesthetic gas and $CO_2$ should be configured to coordinate with any other gas treatment modules. Gas circuits may also need to be connected when necessary. For example, a hose may be used for connecting the gas sampling circuit for anesthetic gas in the gas concentration monitoring module for anesthetic gas and $CO_2$ with an oxygen sampling circuit in the oxygen concentration monitoring module. All of these may lead to a complicated structure, bulky equipment size and inconvenient operation.

SUMMARY OF THIS DISCLOSURE

This disclosure provides medical equipment for gas monitoring that can simplify connection structures between gas circuits and can be integrated with a variety of gas monitoring functions.

In one aspect, a medical equipment for gas monitoring can include a gas treatment system including a first gas monitoring module and an integrated gas circuit board. A first gas circuit that may be a through passage with both inlet and outlet can be arranged inside the integrated gas circuit board. A gas outlet, at least one gas inlet and at least one monitoring interface can be arranged on a surface of the integrated gas circuit board. The gas inlet may include a first gas inlet, and the first gas inlet and the gas outlet can respectively communicate with two ends of the first gas circuit. The monitoring interface may include a first monitoring interface that allows the first gas circuit to communicate to the first gas monitoring module. The monitoring interface may also include an internal gas inlet interface and an internal gas outlet interface that allow the first gas circuit to communicate to a second internal gas monitoring module.

In some embodiments, the gas treatment system may also include a gas circuit switching member having two through-type switching gas circuits. When the first gas circuit communicates with the second internal gas monitoring module, the internal gas inlet interface and the internal gas outlet interface may respectively communicate to the second internal gas monitoring module through the two switching gas circuits.

In some embodiments, the gas treatment system may also include a gas circuit communication member having a through-type shorting gas circuit. The monitoring interface can further include an external gas inlet interface and an external gas outlet interface that allow the first gas circuit to communicate to a second external gas monitoring module. When the first gas circuit communicates with the second internal gas monitoring module, the external gas inlet interface and the external gas outlet interface may communicate with each other through the shorting gas circuit of the gas circuit communication member. When the first gas circuit communicates with the second external gas monitoring module, the internal gas inlet interface and the internal gas outlet interface may communicate with each other through the shorting gas circuit of the gas circuit communication member.

In some embodiments, the medical equipment may further include a housing in which the gas treatment system can be mounted.

In some embodiments, the second internal gas monitoring module can also be mounted inside the housing.

In some embodiments, the gas outlet, the at least one gas inlet, the external gas inlet interface and the external gas outlet interface can be arranged side by side on a same end of the integrated gas circuit board and exposed outside the housing.

In some embodiments, the gas circuit switching member can be a gas circuit switching board for fixing the second internal gas monitoring module. A switching gas inlet, a switching gas outlet, a gas inlet for the monitoring module and a gas outlet for the monitoring module can be arranged on a surface of the gas circuit switching board, and the two switching gas circuits can be arranged inside the gas circuit switching board. The switching gas inlet and the gas inlet for the monitoring module may respectively communicate with two ends of one switching gas circuit, while the switching gas outlet and the gas outlet for the monitoring module may respectively communicate with two ends of the other switching gas circuit.

In some embodiments, the gas circuit communication member can be a gas circuit communication board. A communication gas inlet and a communication gas outlet can be arranged on a surface of the gas circuit communication board, and a communication gas circuit can be arranged inside the gas circuit communication board. Here, the communication gas inlet and the communication gas outlet may respectively communicate with two ends of the communication gas circuit.

In some embodiments, the medical equipment for gas monitoring can be an anesthesia equipment, the first gas monitoring module can be a gas concentration monitoring module for anesthetic gas and carbon dioxide, and the second internal gas monitoring module can be an internal oxygen concentration monitoring module.

In some embodiments, the gas treatment system may also include at least a third gas monitoring module and a master control module. The master control module may be respectively coupled to the first gas monitoring module, the second internal gas monitoring module, and the third gas monitoring module, so as to control the three monitoring modules. At least one second gas circuit that may be a blind passage with one open end can be arranged on a surface of the integrated gas circuit board. The gas inlet can further include a second gas inlet, and the second gas inlet can communicate with the open end of the second gas circuit. The monitoring interface can further comprise a third monitoring interface that allows the first gas circuit to communicate to the third gas monitoring module.

In another aspect, a medical equipment for gas monitoring can include a gas treatment system including a first gas monitoring module and an integrated gas circuit board. A first gas circuit that may be a through passage with both an inlet and an outlet can be arranged inside the integrated gas circuit board. A gas outlet, at least one gas inlet and at least one monitoring interface can be arranged on a surface of the integrated gas circuit board. The gas inlet may include a first gas inlet, and the first gas inlet and the gas outlet can respectively communicate with two ends of the first gas circuit. The monitoring interface may include a first monitoring interface that allows the first gas circuit to communicate to the first gas monitoring module. The monitoring interface may also include an external gas inlet interface and an external gas outlet interface that allow the first gas circuit to communicate to a second external gas monitoring module.

This summary is provided to introduce a selection of concepts that are further described below in the detailed description. This summary is not intended to identify key or essential features of the claimed subject matter, nor is it intended to be used as an aid in limiting the scope of the claimed subject matter.

BRIEF DESCRIPTION OF THE DRAWINGS

The following detailed descriptions of respective embodiments in this disclosure can be understood better when combined with the following figures.

DETAILED DESCRIPTION

Figure 1:
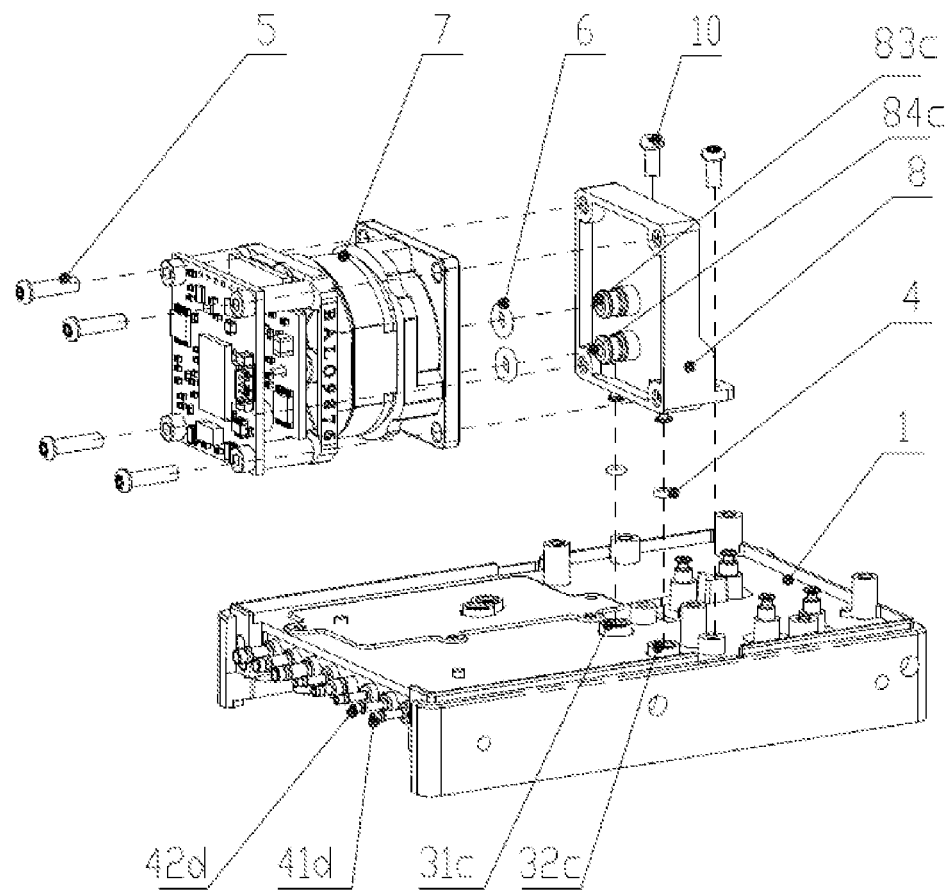
FIG. 1 is an exploded structural diagram for a gas treatment system provided with a second internal gas monitoring module according to an embodiment of this disclosure.

This disclosure is further described below with reference to figures and specific embodiments.

Various embodiments of this disclosure can provide medical equipment for gas monitoring, where the medical equipment may be provided with a gas treatment system that can use gas circuits in an integrated gas circuit board to control the direction of the gas flow so as to sample the gas to be monitored in real time. The gas circuits inside the integrated gas circuit board may communicate with a gas monitoring module through a first monitoring interface, and may also communicate with another gas monitoring module through an internal/external gas inlet interface and an internal/external gas outlet interface. In this approach, the simplified gas circuit structure can be achieved, equipment size can be reduced, and the gas circuits can be conveniently connected by reducing the amount of hose used for gas circuit connections. Moreover, two different gas monitoring modules can be incorporated together in an internal or external fashion so as to implement at least two kinds of gas monitoring.

Due to differences in equipment size, operation environment, or operation mode, gas monitoring modules must be designed in a variety of sizes. For example, for the same kind of gas monitoring module, some manufacturers make the gas monitoring module small so that it can be internally installed on another gas monitoring module, while other manufacturers make the gas monitoring module large so that it can only be externally installed and further connected with another gas monitoring module through a gas pipeline. Here, the smaller gas monitoring module may be defined as a second internal gas monitoring module that can be directly installed inside a first gas monitoring module for cooperative operation, while the larger gas monitoring module may be defined as a second external gas monitoring module that can be externally installed and connected with a first gas monitoring module for cooperative operation.

In an embodiment, a gas treatment system can include a first gas monitoring module and an integrated gas circuit board. It is noted that the medical equipment or the gas treatment system may also be equipped with a gas circuit switching member and a second internal gas monitoring module as needed.

A gas outlet, at least one gas inlet and at least one monitoring interface can be arranged on a surface of the integrated gas circuit board, and a first gas circuit can be arranged inside the integrated gas circuit board. The gas inlet may include a first gas inlet, the first gas circuit may be a through passage with both inlet and outlet, and the first gas inlet and the gas outlet can respectively communicate with two ends of the first gas circuit. The monitoring interface can include a first monitoring interface, an internal gas inlet interface and an internal gas outlet interface. The first gas circuit can communicate to the first gas monitoring module through the first monitoring interface, and to the second internal gas monitoring module through the internal gas inlet interface and the internal gas outlet interface. The gas circuit switching member can include two through-type switching gas circuits. When the first gas circuit communicates to the second internal gas monitoring module, the internal gas inlet interface and the internal gas outlet interface may both communicate to the second internal gas monitoring module via the two switching gas circuits. Based on the descriptions above, the gas to be monitored can first flow into the first gas circuit through the first gas inlet under the action of a gas pump and then flow out of the gas outlet after being monitored by the first gas monitoring module and the second internal gas monitoring module. In some embodiments, in order to reduce the equipment size, the second internal gas monitoring module can be affixed on the integrated gas circuit board by the gas circuit switching member.

In another embodiment, the medical equipment for gas monitoring or the gas treatment system may also include a gas circuit communication member having a through-type shorting gas circuit. The monitoring interface can further include an external gas inlet interface and an external gas outlet interface. In some embodiments, the first gas circuit can selectively communicate to the second internal gas monitoring module through the internal gas inlet interface and the internal gas outlet interface, in which case the gas circuit communication member can be detachably connected between the external gas inlet interface and the external gas outlet interface, so that the two interfaces can directly communicate with each other through the shorting gas circuit. In some embodiments, the first gas circuit can selectively communicate to a second external gas monitoring module through the external gas inlet interface and the external gas outlet interface, in which case the gas circuit communication member can be detachably connected between the internal gas inlet interface and the internal gas outlet interface, so that the two interfaces can directly communicate with each other through the shorting gas circuit. The second internal and/or external gas monitoring module can be selectively configured based on a user's requirement. The gas treatment system in this embodiment can be flexible in operation and suitable for gas monitoring modules having various sizes. Based on the descriptions above, the gas to be monitored can first flow into the first gas circuit through the first gas inlet under the action of a gas pump and then flow out of the gas outlet after being successively monitored by the first gas monitoring module, the second internal gas monitoring module and/or the second external gas monitoring module. The gas circuit communication member described herein can be a gas pipeline made of plastic or metal, and it can also be a gas circuit communication board with a built-in shorting gas circuit.

The integrated gas circuit board may be a board-shaped member made of metal or plastic. For example, two boards with recesses can be affixed together via ultrasonic welding, laser welding or bonding to form the integrated gas circuit board. In this approach, the gas circuits can be constructed by combining the corresponding recesses on the two boards. Alternatively, sealing material can be filled between the two boards to form the gas circuits. In an implementation, a main body of the gas treatment system may be configured as a laminated structure. The gas treatment system can include a circuit board and the integrated gas circuit board where the two boards are laminated together. The circuit board may be disposed on a surface of the integrated gas circuit board where the monitoring interface is arranged. A master control module can be mounted on the circuit board, while a power supply circuit, signal processing circuit, signal sampling and sensing module for gas pressure and the like can also be incorporated onto the circuit board to provide power, signal sampling, data calculation, data output, etc. The circuit board and the integrated gas circuit board may be mounted side by side, which can lead to a more compact equipment structure, thereby reducing both size and power consumption of the equipment. To further reduce the overall equipment size, other gas treatment module(s) or device(s) such as a sensor, oxygen concentration monitoring module and three-way valve can also be affixed onto the integrated gas circuit board or the circuit board. Each gas monitoring module may be provided with a signal interface and a gas circuit interface, where the signal interface can communicate with the master control module via signals. Here, a wired or wireless connection can be used between the signal interface and the master control module; i.e., the signal interface and the master control module can communicate over a wired or wireless connection. The gas circuit interface may be sealingly connected to a corresponding monitoring interface of the integrated gas circuit board so as to implement corresponding gas treatment.

Figure 2:
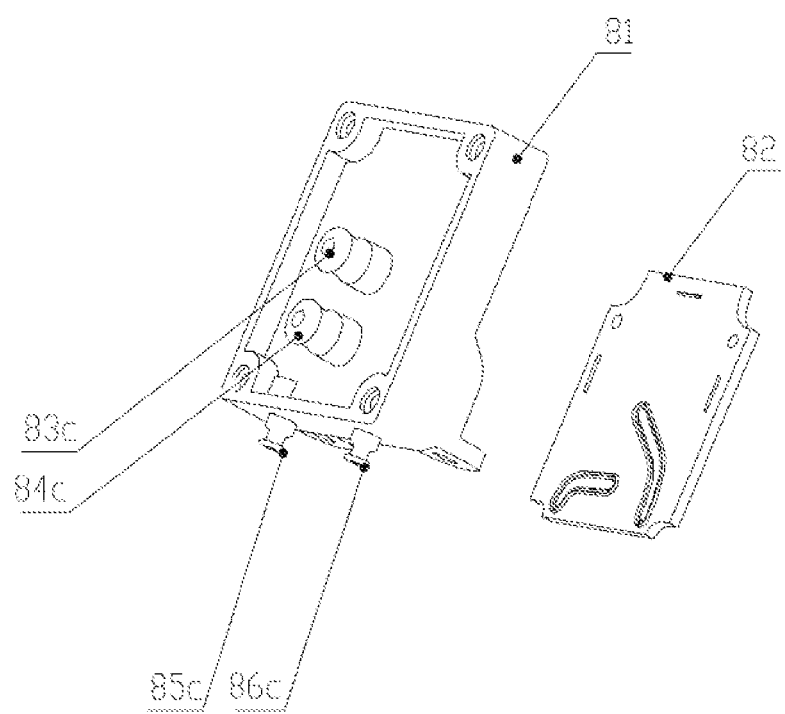
FIG. 2 is an exploded structural diagram for a gas circuit switching board according to an embodiment of this disclosure.
Figure 5:
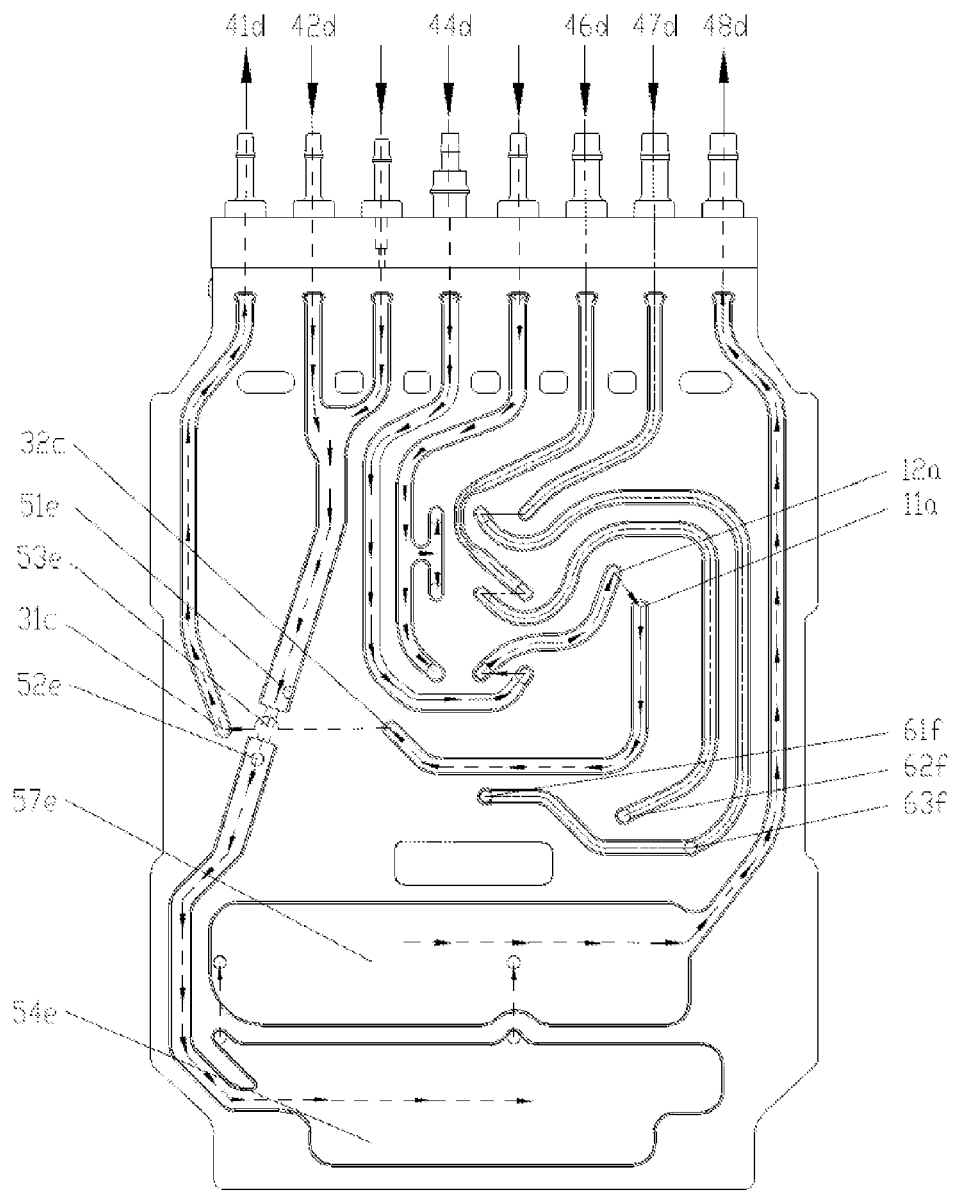
FIG. 5 is a schematic diagram illustrating the flowing of gas in the gas circuits of an integrated gas circuit board according to an embodiment of this disclosure.

Referring now to FIGS. 1, 2 and 5, the medical equipment including the gas treatment system can be an anesthesia equipment or a monitoring equipment by way of example. The gas treatment system may operate to treat the gas in a patient's breathing circuit. For instance, it may perform gas concentration monitoring, respiratory mechanics parameter monitoring and the like. The first gas monitoring module may be a gas concentration monitoring module for anesthetic gas and $CO_2$ that can be used to monitor an anesthetic gas concentration and a $CO_2$ concentration. The second gas monitoring module may be an oxygen concentration monitoring module that can be used to monitor an oxygen concentration. In this embodiment, a first gas inlet 44d and a gas outlet 48d can be disposed on an end of the integrated gas circuit board 1, and a first gas circuit can be disposed inside the integrated gas circuit board 1. The first gas circuit can be a gas sampling circuit. Since the gas in the patient's breathing circuit should be sampled in real time to monitor the gas concentration, the first gas circuit should be a through gas-flow passage, and its inlet and outlet can communicate with the first gas inlet 44d and the gas outlet 48d of the integrated gas circuit board 1 respectively. As shown in FIG. 5, the dashed lines with arrows represent the first gas circuit (i.e., the gas sampling circuit), which can communicate with both the oxygen concentration monitoring module and the gas concentration monitoring module for anesthetic gas and $CO_2$ in series through corresponding monitoring interface(s), so that the oxygen concentration monitoring module and the gas concentration monitoring module for anesthetic gas and $CO_2$ can perform their respective gas concentration monitoring after successively extracting some gas samples from the first gas circuit. The gas circuit interface for the gas concentration monitoring module for anesthetic gas and $CO_2$ can be a group of GMB probes, and their corresponding monitoring interfaces on the surface of the integrated gas circuit board 1 can include a GMB gas inlet 12a and a GMB gas outlet 11a. Based on the size requirement, the oxygen concentration monitoring module can be selected from an internal or external oxygen concentration monitoring module 3. In different situations, corresponding monitoring interfaces on the surface of the integrated gas circuit board 1 can be an internal gas inlet interface 32c and an internal gas outlet interface 31c, and/or an external gas inlet interface 41d and an external gas outlet interface 42d.

The gas treatment system in this embodiment can include a second internal gas monitoring module (specifically, an internal oxygen concentration monitoring module 7). Due to its small size, the internal oxygen concentration monitoring module 7 can be affixed onto the integrated gas circuit board 1 by a gas circuit switching board 8, and a gas circuit interface of the internal oxygen concentration monitoring module 7 can communicate to the internal gas inlet interface 32c on the integrated gas circuit board 1 through one switching gas circuit in the gas circuit switching board 8, while another gas circuit interface of the internal oxygen concentration monitoring module 7 can communicate to the internal gas outlet interface 31c through the other switching gas circuit. In this case, the external gas inlet interface 41d and the external gas outlet interface 42d may be in short connection with each other via the gas circuit communication member. Here, a gas pipeline or a gas circuit communication board can be used as the gas circuit communication member for enabling the communication between the external gas inlet interface 41*d* and the external gas outlet interface 42*d* by the shorting gas circuit therein.

In this embodiment, the gas circuit switching board 8 can include a housing 81 and a gas circuit board 82. The housing 81 and the gas circuit board 82 can be affixed together by screws and sealing material. Alternatively, they may also be affixed together via ultrasonic welding, adhesive bonding or laser welding. A switching gas inlet 86*c*, a switching gas outlet 85*c*, a gas inlet for monitoring module 83*c* and a gas outlet for monitoring module 84*c* may be provided on a surface of the housing 81, and two switching gas circuits may be disposed inside the gas circuit board 82. The switching gas inlet 86*c* and the gas inlet for monitoring module 83*c* may respectively communicate with two ends of one switching gas circuit, and the switching gas outlet 85*c* and the gas outlet for monitoring module 84*c* may respectively communicate with two ends of the other switching gas circuit. If the internal oxygen concentration monitoring module 7 needs to be installed, the external gas inlet interface 41*d* and the external gas outlet interface 42*d* on the integrated gas circuit board 1 may first be in short connection with each other by a gas circuit communication member, such as a gas pipeline or a gas circuit communication board, and then the internal oxygen concentration monitoring module 7 may be affixed onto the gas circuit switching board 8 by a screw 5 while allowing its two gas circuit interfaces to sealingly communicate with the gas inlet for monitoring module 83*c* and the gas outlet for monitoring module 84*c* through sealing rings 6. The gas circuit switching board 8 may in turn be affixed on the integrated gas circuit board 1 by a screw 10, so that the switching gas inlet 86*c* and the switching gas outlet 85*c* can respectively communicate with the internal gas inlet interface 32*c* and the internal gas outlet interface 31*c* and seal therebetween through sealing rings 4. In another embodiment, the gas circuit switching board 8 can be an integral structure, and it may be detachably connected to the integrated gas circuit board 1. The internal oxygen concentration monitoring module 7 can be fixedly arranged on the gas circuit switching board 8 via welding.

In this embodiment, the gas may flow in the gas sampling circuit according to the following sequences:

The first gas inlet 44*d*→the three-way valve→the GMB probe through the GMB gas inlet 12*a* and the GMB gas outlet 11*a*→the internal oxygen concentration monitoring module 7 through the internal gas inlet interface 32*c*, the gas circuit switching board 8 and the internal gas outlet interface 31*c*→the gas pipeline through the external gas inlet interface 41*d* and the external gas outlet interface 42*d*→a flow limiter for gas sampling circuit 53*e* and the differential pressure sensors 51*e*, 52*e*→a first gas container 54*e*→a first gas pump unit and a second gas pump unit→a second gas container 57*e*→the gas outlet 48*d*.

Figure 3:
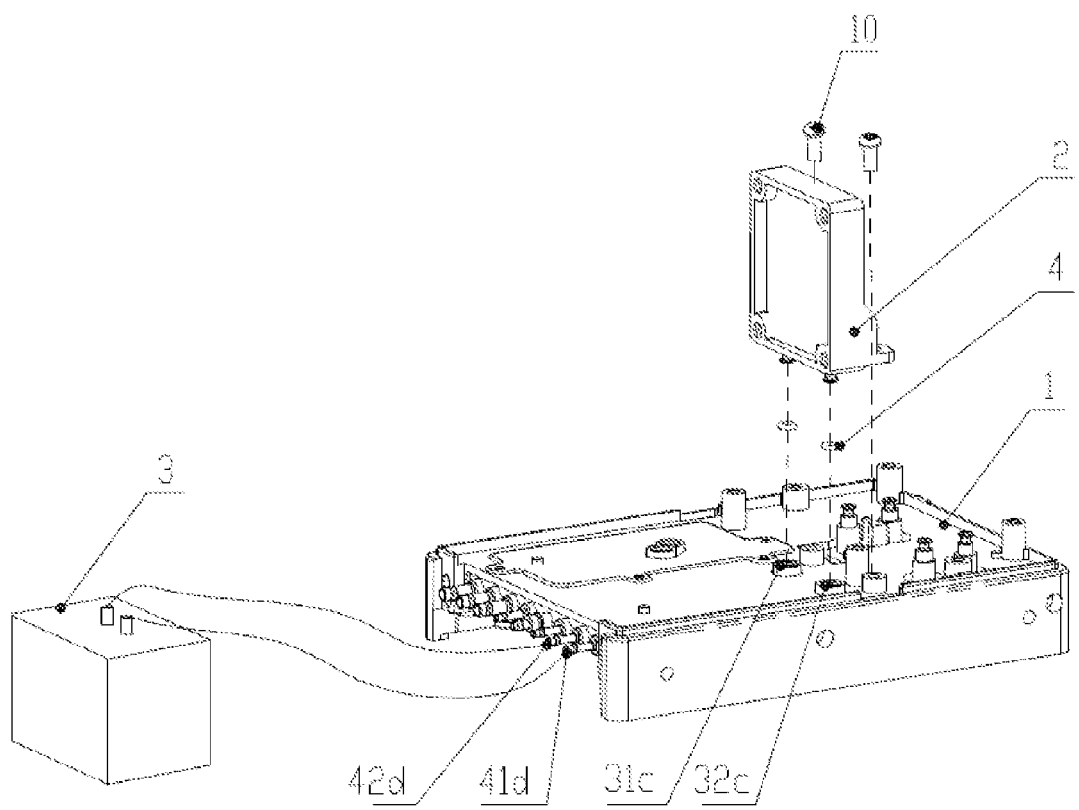
FIG. 3 is an exploded structural diagram for a gas treatment system provided with a second external gas monitoring module according to an embodiment of this disclosure.
Figure 4:
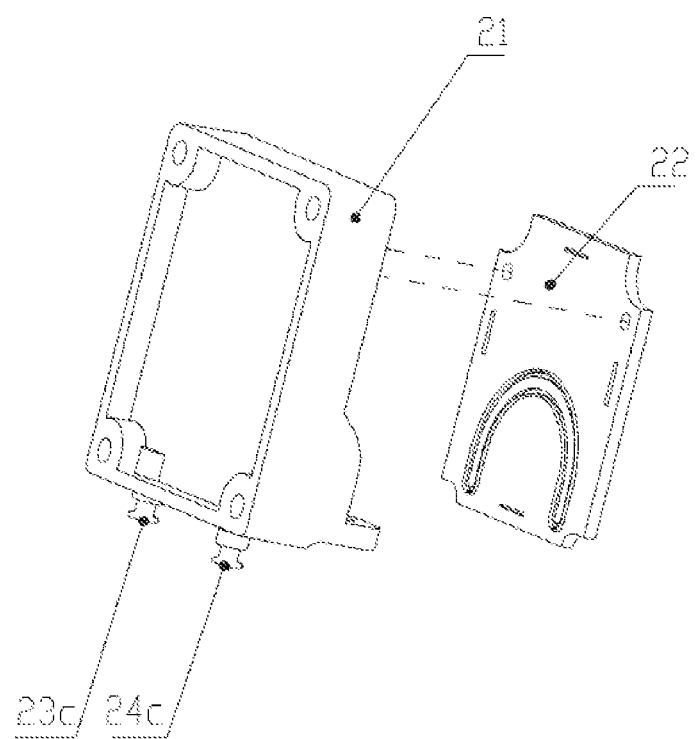
FIG. 4 is an exploded structural diagram for a gas circuit communication board according to an embodiment of this disclosure.

FIGS. 3-5 show another embodiment of this disclosure, where the gas treatment system may instead include a second external gas monitoring module (e.g., an external oxygen concentration monitoring module 3). The second external gas monitoring module may be connected with the integrated gas circuit board 1 by a gas pipeline with a certain length due to its large size. The gas circuit communication member may be a gas circuit communication board 2, and the internal gas inlet interface 32*c* and the internal gas outlet interface 31*c* can be in short connection (i.e., direct communication) with each other through a shorting gas circuit of the gas circuit communication board 2. The gas circuit communication board 2 can include a housing 21 and a gas circuit board 22. The housing 21 and the gas circuit board 22 may be connected together via ultrasonic welding. Alternatively, they can also be affixed together via screws, laser welding or adhesive bonding. A communication gas inlet 24*c* and a communication gas outlet 23*c* can be arranged on a surface of the housing 21, and a shorting gas circuit can be arranged inside the gas circuit board 22, where two ends of the shorting gas circuit can directly communicate with the communication gas inlet 24*c* and the communication gas outlet 23*c*. If the external oxygen concentration monitoring module 3 needs to be installed, two gas pipelines may first be used to sealingly connect the gas circuit interfaces of the external oxygen concentration monitoring module 3 with the external gas inlet interface 41*d* and the external gas outlet interface 42*d*. Subsequently, the gas circuit communication board 2 may be affixed on the integrated gas circuit board 1 by a screw 10, so that the communication gas inlet 24*c* and the communication gas outlet 23*c* may respectively communicate with the internal gas inlet interface 32*c* and the internal gas outlet interface 31*c* via a sealing ring 4. In another embodiment, the gas circuit communication board 2 can be designed as an integral structure, or be detachably connected with the integrated gas circuit board 1, for example be releasing a clip assembly or other clip structure.

In this embodiment, the gas may flow in the gas sampling circuit according to the following sequences:

The first gas inlet 44*d*→the three-way valve→the GMB probe through the GMB gas inlet 12*a* and the GMB gas outlet 11*a*→the gas circuit communication board 2 through the internal gas inlet interface 32*c* and the internal gas outlet interface 31*c*→the external oxygen concentration monitoring module 3 through the external gas inlet interface 41*d* and the external gas outlet interface 42*d*→a flow limiter for gas sampling circuit 53*e* and the differential pressure sensors 51*e*, 52*e*→the first gas container 54*e*→the first gas pump unit and the second gas pump unit→the second gas container 57*e*→the gas outlet 48*d*.

In some embodiments, the gas treatment system may be equipped with the gas circuit switching board 8 and the gas circuit communication board 2 simultaneously. Both the gas circuit switching board 8 and the gas circuit communication board 2 can be detachably connected with the integrated gas circuit board 1 and can be selectively used by the user according to specific needs during operation.

In some embodiments, the first gas monitoring module can operate to monitor any other gas concentration or any other gas characteristics. The second external/internal gas monitoring module can be an external/internal gas concentration monitoring module for anesthetic gas and $CO_2$ or any other external/internal gas monitoring module. In some embodiments, there can be multiple first gas monitoring modules and second internal/external gas monitoring modules, and there may also be multiple external gas inlet interfaces, external gas outlet interfaces, internal gas inlet interfaces, internal gas outlet interfaces, gas circuit communication members and gas circuit switching members. In this situation, the multiple first gas monitoring modules and the multiple second internal/external gas monitoring modules can communicate with the first gas circuit in series through corresponding monitoring interfaces. Moreover, the multiple second internal gas monitoring modules can be affixed on the integrated gas circuit board to reduce the equipment size.

In an embodiment, the medical equipment may also include a housing which may be a specialized member or the housing of the first gas monitoring module. The first gas monitoring module and the integrated gas circuit board may both be mounted within a specialized housing, or the integrated gas circuit board may be mounted within the housing of the first gas monitoring module. As needed, the second internal gas monitoring module can also be mounted within the housing to achieve a smaller and more compact structure for the entire equipment. For example, the internal oxygen concentration monitoring module 7 and the integrated gas circuit board 1 can be internally installed within the housing of the gas concentration monitoring module for anesthetic gas and $CO_2$, and as a result the oxygen concentration monitoring function can be incorporated without increasing the size of the gas concentration monitoring module for anesthetic gas and $CO_2$, thereby reducing the equipment size. In another embodiment shown in FIG. 5, the gas outlet 48d, at least one gas inlet, the external gas inlet interface 41d and the external gas outlet interface 42d can be arranged side by side on a same end of the integrated gas circuit board 1 and exposed outside the housing to facilitate their connection with corresponding gas circuits. In another embodiment, when the second internal gas monitoring module is mounted outside the housing, the internal gas inlet interface 32c and the internal gas outlet interface 31c may be exposed outside the housing; when the second internal gas monitoring module is mounted inside the housing, there is no need to expose the internal gas inlet interface 32c and the internal gas outlet interface 31c outside the housing.

In an embodiment, the gas treatment system may also include at least a third gas monitoring module. The master control module can be respectively coupled to the first gas monitoring module, the second internal/external gas monitoring module and the third gas monitoring module to control the three modules. At least one second gas circuit that may be a blind passage with one open end can be arranged inside the integrated gas circuit board. The gas inlet can further include a second gas inlet in communication with the open end of the second gas circuit. The monitoring interface may further include a third monitoring interface, and the second gas circuit can communicate with the third gas monitoring module through the third monitoring interface. In this approach, the gas to be monitored can first flow into the second gas circuit through the second gas inlet, and then be monitored by the third gas monitoring module, such that the gas within the second gas circuit can be prevented from communicating with and being interfered by external gas flow. In the embodiment shown in FIG. 5, second gas inlets 46d, 47d and a zero calibration gas inlet can further be arranged on a surface of the integrated gas circuit board 1 as needed, while a second gas circuit and a zero calibration gas circuit can be arranged inside the integrated gas circuit board 1. The second gas circuit can include two independent respiratory mechanics gas circuits indicated by the dashed lines in FIG. 5 which are separated from the gas sampling circuit. The third gas monitoring module can be a respiratory mechanics monitoring module that may include a pressure sensor and a differential pressure sensor. The monitoring interface on the surface of the integrated gas circuit board 1, which can be arranged to communicate with the respiratory mechanics gas circuit, may include a pressure sensor interface 61f and two differential pressure sensor interfaces. The pressure sensor interface 61f may communicate to one respiratory mechanics gas circuit, the pressure sensor may be pressed with the pressure sensor interface 61f, and a gas circuit interface of the pressure sensor 3 may be sealingly engaged with the pressure sensor interface 61f. Each differential pressure sensor interface can include a first differential pressure sampling port 62f and a second differential pressure sampling port 63f, where the two differential pressure sampling ports can respectively communicate to the two respiratory mechanics gas circuits. The differential pressure sensors 51e, 52e may be pressed with the two differential pressure sensor interfaces, and their gas circuit interfaces may also be sealingly engaged with the two differential pressure sensor interfaces. In some embodiments, the third gas monitoring module can also operate to monitor any other gas characteristics.

The medical equipment in various embodiments of this disclosure can be an anesthesia equipment or a monitoring equipment. For the gas treatment system in the medical equipment herein, its gas circuits can be connected without using any hose. Also, at least two kinds of gas monitoring are available by internally or externally integrating a different kind of gas monitoring module onto one kind of gas monitoring module. As a result, the medical equipment can be simple and compact in both functionality and structure, the size of the medical equipment can be reduced, and the medical equipment can be conveniently and flexibly operated to facilitate its clinical application.

This disclosure is described above with detailed illustrations and reference to specific implementations, although it should not be limited to these illustrations. For those of ordinary skill in the art, various conclusions or equivalents may be made without departing from the concept of this disclosure, while such conclusions or equivalents should be deemed to be included within the scope of this disclosure.

The invention claimed is:

1. A medical equipment for gas monitoring comprising a gas treatment system, wherein the gas treatment system comprises:
    a first gas monitoring module; and
    an integrated gas circuit board, wherein the integrated gas circuit board comprises:
        a first gas circuit arranged inside the integrated gas circuit board, wherein the first gas circuit is a through passage with both inlet and outlet;
        a gas outlet, at least one gas inlet and at least one monitoring interface arranged on a surface of the integrated gas circuit board; wherein the gas inlet comprises a first gas inlet, and the first gas inlet and the gas outlet respectively communicate with two ends of the first gas circuit; the monitoring interface comprises a first monitoring interface that allows the first gas circuit to communicate to the first gas monitoring module; wherein the monitoring interface further comprises an internal gas inlet interface and an internal gas outlet interface that allow the first gas circuit to be capable of communicating to a second internal gas monitoring module;
    the medical equipment further comprises a gas circuit switching member; wherein the gas circuit switching member comprises two through-type switching gas circuits; when the first gas circuit communicates with the second internal gas monitoring module, the internal gas inlet interface and the internal gas outlet interface respectively communicate to the second internal gas monitoring module through the two switching gas circuits;
    the medical equipment further comprises a gas circuit communication member having a through-type shorting gas circuit;
        wherein the monitoring interface further comprises an external gas inlet interface and an external gas outlet interface that allow the first gas circuit to be capable of communicating to a second external gas monitoring module; if the first gas circuit communicates with the second internal gas monitoring module, the external gas inlet interface and the external gas outlet interface communicate with each other through the shorting gas circuit of the gas circuit communication member; if the first gas circuit communicates with the second external gas monitoring module, the internal gas inlet interface and the internal gas outlet interface communicate with each other through the shorting gas circuit of the gas circuit communication member.

2. The medical equipment for gas monitoring of claim 1, further comprising a housing, wherein the gas treatment system is mounted inside the housing.

3. The medical equipment for gas monitoring of claim 2, wherein the second internal gas monitoring module is also mounted inside the housing.

4. The medical equipment for gas monitoring of claim 2, wherein the gas outlet, the at least one gas inlet, the external gas inlet interface and the external gas outlet interface are arranged side by side on a same end of the integrated gas circuit board and exposed outside the housing.

5. The medical equipment for gas monitoring of claim 1, wherein the gas circuit switching member is a gas circuit switching board for fixing the second internal gas monitoring module; a switching gas inlet, a switching gas outlet, a gas inlet for monitoring module and a gas outlet for monitoring module are arranged on a surface of the gas circuit switching board, and the two switching gas circuits are arranged inside the gas circuit switching board; the switching gas inlet and the gas inlet for monitoring module respectively communicate with two ends of one switching gas circuit, while the switching gas outlet and the gas outlet for monitoring module respectively communicate with two ends of the other switching gas circuit.

6. The medical equipment for gas monitoring of claim 1, wherein the gas circuit communication member is a gas circuit communication board; a communication gas inlet and a communication gas outlet are arranged on a surface of the gas circuit communication board, and a communication gas circuit is arranged inside the gas circuit communication board; wherein the communication gas inlet and the communication gas outlet respectively communicate with two ends of the communication gas circuit.

7. The medical equipment for gas monitoring of claim 1, wherein the medical equipment for gas monitoring is an anesthesia equipment, the first gas monitoring module is a gas concentration monitoring module for anesthetic gas and carbon dioxide, and the second internal gas monitoring module is an internal oxygen concentration monitoring module.

8. A medical equipment for gas monitoring comprising a gas treatment system, wherein the gas treatment system comprises:
a first gas monitoring module; and
an integrated gas circuit board, wherein the integrated gas circuit board comprises:
 a first gas circuit arranged inside the integrated gas circuit board, wherein the first gas circuit is a through passage with both inlet and outlet;
 a gas outlet, at least one gas inlet and at least one monitoring interface arranged on a surface of the integrated gas circuit board; wherein the gas inlet comprises a first gas inlet, and the first gas inlet and the gas outlet respectively communicate with two ends of the first gas circuit; the monitoring interface comprises a first monitoring interface that allows the first gas circuit to communicate to the first gas monitoring module; wherein the monitoring interface further comprises an internal gas inlet interface and an internal gas outlet interface that allow the first gas circuit to be capable of communicating to a second internal gas monitoring module;
wherein said gas treatment system further comprises:
 at least one third gas monitoring module;
 a master control module respectively coupled to the first gas monitoring module, the second internal gas monitoring module and the third gas monitoring module so as to control said three monitoring modules;
wherein at least one second gas circuit that is a blind passage with one open end is arranged on a surface of the integrated gas circuit board; the gas inlet further comprises a second gas inlet, and the second gas inlet communicates with the open end of the second gas circuit; the monitoring interface further comprises a third monitoring interface that allows the first gas circuit to communicate to the third gas monitoring module.

9. A medical equipment for gas monitoring comprising a gas treatment system, wherein the gas treatment system comprises:
a first gas monitoring module,
an integrated gas circuit board, wherein the integrated gas circuit board comprises:
a first gas circuit arranged inside the integrated gas circuit board, wherein the first gas circuit is a through passage with both inlet and outlet;
a gas outlet, at least one gas inlet and at least one monitoring interface arranged on a surface of the integrated gas circuit board; wherein the gas inlet comprises a first gas inlet, and the first gas inlet and the gas outlet respectively communicate with two ends of the first gas circuit; the monitoring interface comprises a first monitoring interface that allow the first gas circuit to communicate to the first gas monitoring module; wherein the monitoring interface further comprises an external gas inlet interface and an external gas outlet interface that allow the first gas circuit to be capable of communicating to a second external gas monitoring module; the monitoring interface further comprises an internal gas inlet interface and an internal gas outlet interface that allow the first gas circuit to be capable of communicating to a second internal gas monitoring module;
wherein the medical equipment further comprises a gas circuit communication member having a through-type shorting gas circuit;
if the first gas circuit communicates with the second internal gas monitoring module, the external gas inlet interface and the external gas outlet interface communicate with each other through the shorting gas circuit of the gas circuit communication member; if the first gas circuit communicates with the second external gas monitoring module, the internal gas inlet interface and the internal gas outlet interface communicate with each other through the shorting gas circuit of the gas circuit communication member.

10. The medical equipment for gas monitoring of claim 9, wherein the gas outlet, the at least one gas inlet, the external gas inlet interface and the external gas outlet interface are arranged side by side on a same end of the integrated gas circuit board and exposed outside the housing.

11. The medical equipment for gas monitoring of claim 9, wherein the medical equipment further comprises a gas circuit switching member; wherein the gas circuit switching member comprises two through-type switching gas circuits; when the first gas circuit communicates with the second internal gas monitoring module, the internal gas inlet interface and the internal gas outlet interface respectively communicate to the second internal gas monitoring module through the two switching gas circuits.

12. The medical equipment for gas monitoring of claim 11, wherein the gas circuit switching member is a gas circuit switching board for fixing the second internal gas monitoring module; a switching gas inlet, a switching gas outlet, a gas inlet for monitoring module and a gas outlet for monitoring module are arranged on a surface of the gas circuit switching board, and the two switching gas circuits are arranged inside the gas circuit switching board; the switching gas inlet and the gas inlet for monitoring module respectively communicate with two ends of one switching gas circuit, while the switching gas outlet and the gas outlet for monitoring module respectively communicate with two ends of the other switching gas circuit.

13. The medical equipment for gas monitoring of claim 9, wherein the gas circuit communication member is a gas circuit communication board; a communication gas inlet and a communication gas outlet are arranged on a surface of the gas circuit communication board, and a communication gas circuit is arranged inside the gas circuit communication board; wherein the communication gas inlet and the communication gas outlet respectively communicate with two ends of the communication gas circuit.

14. The medical equipment for gas monitoring of claim 9, wherein the medical equipment for gas monitoring is an anesthesia equipment, the first gas monitoring module is a gas concentration monitoring module for anesthetic gas and carbon dioxide, and the second internal gas monitoring module is an internal oxygen concentration monitoring module.

15. The medical equipment for gas monitoring of claim 9, wherein said gas treatment system further comprises:
   at least one third gas monitoring module;
   a master control module respectively coupled to the first gas monitoring module, the second internal gas monitoring module and the third gas monitoring module so as to control said three monitoring modules;
   wherein at least one second gas circuit that is a blind passage with one open end is arranged on a surface of the integrated gas circuit board; the gas inlet further comprises a second gas inlet, and the second gas inlet communicates with the open end of the second gas circuit; the monitoring interface further comprises a third monitoring interface that allows the first gas circuit to communicate to the third gas monitoring module.

* * * * *